United States Patent [19]

Hirsch et al.

[11] Patent Number: 4,602,025

[45] Date of Patent: Jul. 22, 1986

[54] AROMATASE INHIBITORS

[75] Inventors: Kenneth S. Hirsch, New Palestine; Charles D. Jones; Harold M. Taylor, both of Indianapolis, all of Ind.

[73] Assignee: Eli Lilly and Company, Indianapolis, Ind.

[21] Appl. No.: 621,583

[22] Filed: Jun. 18, 1984

[51] Int. Cl.$^4$ ............... A61K 31/40; A61K 31/41; A61K 31/415

[52] U.S. Cl. .................. 514/359; 514/381; 514/385; 514/397; 514/406; 514/422; 514/383; 548/255; 548/250; 548/262; 548/374; 548/518; 548/336

[58] Field of Search ............... 424/269; 548/262, 255, 548/254, 247, 235, 214, 205, 143, 136, 134, 345, 250, 336, 374, 518; 514/359, 385, 386, 383, 397, 381, 406, 383, 422

[56] References Cited

U.S. PATENT DOCUMENTS

| | | | |
|---|---|---|---|
| 2,656,358 | 8/1950 | Sperber et al. | 548/205 |
| 3,709,901 | 1/1973 | Draber et al. | 260/310 R |
| 3,764,690 | 10/1973 | Draber et al. | 424/273 |
| 3,794,653 | 2/1974 | Draber et al. | 260/296 R |
| 3,801,590 | 4/1974 | Draber et al. | 548/247 |
| 3,833,603 | 9/1974 | Buchel et al. | 548/345 |
| 3,836,540 | 9/1974 | Stelt et al. | 548/345 |
| 3,852,056 | 12/1974 | Draber et al. | 71/76 |
| 3,870,726 | 3/1975 | Jager et al. | 548/255 |
| 3,897,438 | 7/1975 | Draber et al. | 548/205 |
| 3,928,348 | 12/1975 | Draber et al. | 548/345 |
| 3,941,800 | 3/1976 | Draber et al. | 548/255 |
| 4,446,145 | 5/1984 | Van Bever | 424/269 |

FOREIGN PATENT DOCUMENTS

| | | | |
|---|---|---|---|
| 765585 | 4/1970 | Belgium | 514/383 |
| 3129193 | 2/1983 | Fed. Rep. of Germany | 548/255 |

*Primary Examiner*—Glennon H. Hollrah
*Assistant Examiner*—Dara L. Dinner
*Attorney, Agent, or Firm*—Robert A. Conrad; Arthur R. Whale

[57] ABSTRACT

This invention provides a method of inhibiting aromatase and treating estrogen-dependent diseases in mammals by administering certain azole derivatives. Certain azole derivatives and their pharmaceutical formulations are also provided.

11 Claims, No Drawings

AROMATASE INHIBITORS

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include estrogen dependent breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research*, supra.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide certain azole derivatives, their pharmaceutical formulations, and their use in a method for inhibiting the enzyme aromatase in mammals. The invention thus provides for the treatment of estrogen dependent breast cancer and other estrogen-dependent diseases.

SUMMARY OF THE INVENTION

This invention provides compounds of the formula

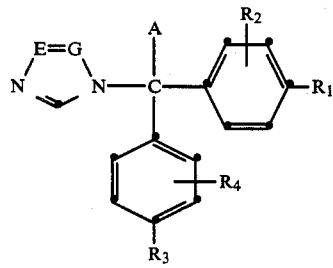

wherein:

A is a 5-membered heterocyclic group containing at least one nitrogen atom beta to the point of attachment selected from the group consisting of 3-pyrrolyl, 4(5)-imidazolyl, 3-pyrazolyl, 4-pyrazolyl, 5-oxazolyl, 5-thiazolyl, 4-isoxazolyl, 5-isoxazolyl, 4-isothiazolyl, 5-isothiazolyl, 4-1,2,3-triazolyl, 3-1,2,4-triazolyl, 5-tetrazolyl, 2-1,3,4-oxadiazolyl, 2-1,3,4-thiadiazolyl, 5-1,2,3-oxadiazolyl, 5-1,2,3-thiadiazolyl, 4-1,2,3-oxadiazolyl, 4-1,2,3-thiadiazolyl, 5-1,2,4-oxadiazolyl, 5-1,2,4-thiadiazolyl, 3-1,2,5-oxadiazolyl, and 3-1,2,5-thiadiazolyl;

E and G are independently N or CH; and $R_1$, $R_2$, $R_3$, and $R_4$ are independently hydrogen, halo, nitro, $C_1$–$C_3$ alkyl, $C_1$–$C_3$ alkoxy, or trifluoromethyl; and pharmaceutically-acceptable salts thereof.

This invention also provides a method of inhibiting aromatase in mammals which comprises administering to said mammal an aromatase inhibiting amount of a compound of the above formula. By virtue of their ability to inhibit the enzyme aromatase, the compounds of the above formula are useful in the treatment of estrogen-dependent diseases, especially estrogen dependent breast cancer, in mammals.

Further provided by this invention are pharmaceutical formulations which comprise a compound of the above formula together with a pharmaceutically-acceptable carrier, excipient, or diluent therefor. These formulations are particularly useful for the treatment of estrogen-dependent diseases, such as estrogen dependent breast cancer.

DETAILED DESCRIPTION AND PREFERRED EMBODIMENT

The term "$C_1$–$C_3$ alkyl" refers to methyl, ethyl, propyl, and isopropyl. The term "$C_1$–$C_3$ alkoxy" refers to methoxy, ethoxy, propoxy, and isopropoxy. The term "halo" refers to fluoro, chloro, bromo, and iodo.

A preferred group of compounds useful in the method of this invention are those wherein:

(a) A is selected from 4(5)-imidazolyl, 3-pyrazolyl, 4-pyrazolyl, 5-isoxazolyl, 5-isothiazolyl, and 3-1,2,4-triazolyl, (b) E is CH, and (c) $R_1$ and $R_3$ are independently halo, especially chloro or fluoro, or triflfuoromethyl.

Especially preferred compounds are those where $R_2$ and $R_4$ are each hydrogen.

As will be recognized by those skilled in the art, many of the compounds of Formula I contain an asymmetric carbon atom. This invention is not limited to any particular isomer but includes the individual enantiomers as well as the racemates of the compounds.

The pharmaceutically acceptable acid addition salts used in this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesuulfonate, naphthalene-1-sulfonate, naphthalene-2-sulfonate and the like salts. The preferred salts of this invention are those derived from inorganic acids, especially hydrochloric acid.

The compounds of this invention may be prepared by any number of methods known in the art. In particular, the compounds of Formula I can be prepared by methods as described in the following U.S. Pat. Nos: 3,709,901, 3,764,690, 3,794,653, 3,897,438, and 3,852,056.

A preferred method of making the compounds of this invention is summarized by the following scheme:

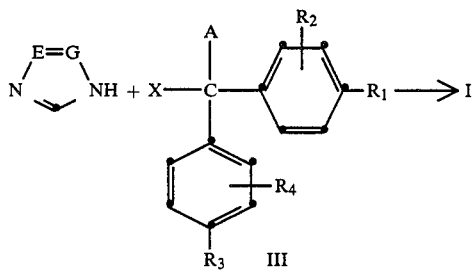

where X is chloro or bromo.

According to the above reaction scheme, azole II is allowed to react with intermediate III, preferably in the presence of a non-reactive solvent such as dioxane, dimethylformamide, or preferably acetonitrile. It is generally preferred that a 2-6 fold molar excess of the azole is used although other ratios are operative. The reaction is carried out at temperatures from about 20° C. up to the reflux temperature of the reaction mixture, for example about 80° C. When the preferred conditions of refluxing acetonitrile are employed, the reaction is generally complete within about 1-6 hours.

Variations on the above reaction can also be employed. For example, an intermediate carbinol III wherein X is hydroxy may be converted to the corresponding chloro or bromo intermediate in situ, for example by reaction with thionyl chloride or thionyl bromide, which is then reacted with azole II. Alternatively, the azole can be treated with thionyl chloride or thionyl bromide following the procedure of U.S. Pat. No. 3,897,438 to prepare an intermediate thionyl-azolide which is then reacted with the carbinol III to provide the desired product I.

Intermediates II and III are either commercially available, are known in the art, or can be prepared by methods known in the art.

In order to more fully illustrate the preparation of the compounds of this invention, the following examples are provided. The examples are illustrative only and are not intended to limit the scope of the invention in any way.

EXAMPLE 1

5-(1H-Imidazol-1-yldiphenylmethyl)isothiazole

Two grams of α,α-diphenyl-5-isothiazolemethanol were heated at reflux for approximately 4 hours with an equimolar amount of thionyl chloride in approximately 20 ml of toluene. The toluene was removed in vacuo and the residue was heated at reflux for 6 hours with 2 grams of imidazole in 50 ml of acetonitrile. The reaction mixture was evaporated in vacuo, taken up in chloroform, washed with water, dried, and evaporated. The residue was suspended in toluene and filtered to provide 1.2 g of the desired title product, m.p. 164°-167° C.

Analysis for $C_{19}H_{15}N_3S$: Calc.: C, 71.90; H, 4.76; N, 13.24; Found: C, 71.97; H, 4.89; N, 13.18.

EXAMPLE 2

5-(Diphenyl-1H-1,2,4-triazol-1-ylmethyl)-isothiazole

Following the procedure of Example 1, 1.5 g of α,α-diphenyl-5-isothiazolemethanol were converted to the corresponding chloro compound and treated with 1.5 g of 1,2,4-triazole to provide 0.5 g of the title product, m.p. 235°-240° C.

EXAMPLE 3

3-[1H-Imidazol-1-yl-bis(4-chlorophenyl)methyl]-1,2,4-triazole

To a stirred solution of 1.7 g of imidazole in 20 ml of acetonitrile were added 0.74 g of thionyl chloride. After 5 minutes, the reaction mixture was filtered and the filtrate was added to 2.0 g of α,α-bis(4-chlorophenyl)-3-1,2,4-triazolemethanol. The filtrate mixture was brought to reflux for 3 hours, cooled, and allowed to stand for 3 days. The resulting crystals were recovered by filtration and recrystallized from methanol to provide 1.01 g of the desired title product, m.p. 188°-191° C.

Analysis for $C_{18}H_{13}Cl_2N_5$: Calc.: C, 58.39; H, 3.54; N, 18.92; Cl, 19.15; Found: C, 58.20; H, 3.80; N, 18.74; Cl, 19.32.

EXAMPLE 4-7

Following the general procedure of Example 3, the following compounds were prepared from the corresponding carbinol and the appropriate azole.

4. 3-[Bis(4-chlorophenyl)-1H-imidazol-1-ylmethyl]-pyrazole, 38% yield, m.p. 214°-216° C.

Analysis for $C_{19}H_{14}Cl_2N_4$: Calc.: C, 61.80; H, 3.82; N, 15.17; Found: C, 61.67; H, 4.06; N, 14.97.

5. 4-[Bis(4-chlorophenyl)-1H-imidazol-1-ylmethyl]-1,2,3-triazole, 25% yield, m.p. 155°-156° C.

Analysis for $C_{18}H_{13}Cl_2N_5$: Calc.: C, 58.39; H, 3.54; N, 18.92; Found: C, 58.64; H, 3.76; N, 18.69.

6. 5-[Bis(4-chlorophenyl)-1H-imidazol-1-ylmethyl]isothiazole, 45% yield, m.p. 148°-150° C.

Analysis for $C_{19}H_{13}Cl_2N_3S$: Calc.: C, 59.07; H, 3.39; N, 10.88; Found: C, 59.04; H, 3.59; N, 11.04.

7. 1-[Bis(4-chlorophenyl)-5-isothiazolemethyl]-1H-1,2,4-triazole, 31% yield, m.p. 146°-148° C.

Analysis for $C_{18}H_{12}Cl_2N_4S$: Calc.: C, 55.82; H, 3.12; N, 14.47; Found: C, 56.09; H, 2.88; N, 14.37.

Following the procedures of Examples 1 or 3, the following compounds can be prepared.

1-[bis(4-chlorophenyl)oxazol-5-ylmethyl]-tetrazole,
1-[(4-trifluoromethylphenyl)(4-fluorophenyl)-pyrazol-3-ylmethyl]-1,2,4-triazole,
4-[(4-bromophenyl)(4-fluorophenyl)-1,2,3-thiadiazol-5-ylmethyl]-1,2,4-triazole,
1-[bis(4-trifluoromethylphenyl)pyrrol-3-ylmethyl]imidazole,
1-[(4-chlorophenyl)(4-iodophenyl)-1,2,4-triazol-3-ylmethyl]-1,2,4-triazole,
4-[bis(4-fluorophenyl)thiazol-5-ylmethyl]-tetrazole,
1-[(4-fluorophenyl)(4-trifluoromethylphenyl)-imidazol-4(5)-ylmethyl]imidazole,
4-[bis(4-chlorophenyl)-1,2,3-triazol-4-ylmethyl]-1,2,4-triazole,
1-[bis(4-chlorophenyl)pyrazol-4-ylmethyl]-imidazole,
1-[(4-chlorophenyl)(4-trifluoromethylphenyl)-isoxazol-5-ylmethyl]tetrazole, 1-[(4-fluorophenyl)(4-iodophenyl)-1,2,3-oxadiazol-5-ylmethyl]imidazole,
1-[bis(4-bromophenyl)-1,3,4-oxadiazol-2-ylmethyl]-1,2,4-triazole,
4-[(4-bromophenyl)(4-iodophenyl)isothiazol-5-ylmethyl]-1,2,4-triazole,
1-[bis(iodophenyl)-1,3,4-thiadiazol-2-ylmethyl]imidazole,
1-[(4-fluorophenyl)(4-trifluoromethylphenyl)-pyrazol-4-yl]imidazole,
4-[(4-chlorophenyl)(4-trifluoromethylphenyl)-1,2,3-triazol-4-ylmethyl]-1,2,4-triazole.

The compounds provided by this invention are useful in therapeutically treating estrogen-dependent diseases, including estrogen dependent breast cancer, in mammals by virtue of their ability to inhibit the enzyme aromatase. Their ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 $\mu$M 4-androstene-3,17-dione, 100,000 dpm 1,2[$^3$H]-androstenedione, the microsomes and a NADPH generating system. The concentrations of the inhibitors tested ranged between 0.005 and 10 $\mu$M. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with control samples incubated without inhibitor. Potency is determined based on the concentration of inhibitor in $\mu$M required to produce a 50% inhibition of enzyme activity (EC$_{50}$) when the concentration of substrate (androstenedione) is 0.1 $\mu$M. The EC$_{50}$'s of certain of the compounds of the above formula are summarized in Table 1.

TABLE 1

| Aromatase Inhibition in the Rat Ovarian Microsome Assay | |
|---|---|
| Compound of Example No. | EC$_{50}$* |
| 1 | <0.05 |
| 2 | 0.257 |
| 3 | <0.05 |
| 4 | 0.061 |
| 5 | <0.05 |
| 6 | 0.057 |
| 7 | 0.051 |

*Concentration of compound in $\mu$M required to achieve 50% inhibition of aromatase activity when substrate concentration is 0.1 $\mu$M.

The compounds may be administered by any number of routes, including the oral, subcutaneous, intramuscular, intravenous, transdermal, and rectal routes. The compounds are usually employed in the form of pharmaceutical compositions. Such compositions are prepared in a manner well known in the pharmaceutical art and comprise at least one active compound of the invention.

Such pharmaceutical compositions comprise as active ingredient from about 1 to about 95% by weight of a compound of the above formula I associated with a pharmaceutically acceptable carrier. In making the compositions, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations can additionally include lubricating agents, wetting agents, emulsifying and suspending agents, preserving agents, sweetening agents or flavoring agents. The compositions may be formulated so as to provide quick, sustained, or delayed release of the active ingredient after administration to the patient by employing procedures well known in the art.

For oral administration, a compound of this invention can be admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.05 to about 300 mg/kg of body weight. In the treatment of adult humans, the range of about 0.1 to about 50 mg/kg, in single or divided doses, is preferred. However, it will be understood that the amount of the compound actually administered will be determined by a physical, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

In order to more fully illustrate the operation of this invention, the following formulation examples are provided. The examples are illustrative only and are not intended to limit the scope of the invention. The formulations employ as active compounds any of the pharmaceutical compounds of the above formula.

EXAMPLE 8

Hard gelatin capsules are prepared using the following ingredients:

| | per capsule |
|---|---|
| 3-[1H—imidazol-1-yl-bis(4-chlorophenyl)methyl]-1,2,4-triazole | 250 mg |
| Starch dried | 200 mg |
| Magnesium stearate | 10 mg |
| Total | 460 mg |

The above ingredients are mixed and filled into hard gelatin capsules in 460 mg quantities.

EXAMPLE 9

Capsules each containing 20 mg of medicament are made as follows:

| | per capsule |
|---|---|
| 3-[bis(4-fluorophenyl)-1H—imidazol-1-ylmethyl]pyrazole | 20 mg |
| Starch | 89 mg |
| Microcrystalline cellulose | 89 mg |
| Magnesium stearate | 2 mg |
| Total | 200 mg | the active ingredient, cellulose, starch and magnesium stearate are blended, passed through a No. 45 mesh U.S. sieve and filled into hard gelatin capsules in 200 mg quantities.

EXAMPLE 10

Capsules each containing 100 mg of active ingredient are made as follows:

| | per capsule |
|---|---|
| 4-[(4-Fluorophenyl)(4-trifluoromethylphenyl)-1H—imidazol-1-yl-methyl]-1,2,3-triazole | 100 mg |
| Polyoxyethylenesorbitan monooleate | 50 mcg |
| Starch powder | 250 mg |

The above ingredients are thoroughly mixed and are placed in an empty gelatin capsule.

EXAMPLE 11

Tablets each containing 10 mg of active ingredient are made up as follows:

| | per tablet |
|---|---|
| 5-[(4-Chlorophenyl)(4-fluorophenyl)-1H—imidazol-1-ylmethyl]-isothiazole | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 12

A tablet formula is prepared using the ingredients below:

| | per tablet |
|---|---|
| 1-[bis(4-fluorophenyl)-1,2,4-triazol-3-ylmethyl]-1,2,4-triazole | 250 mg |
| Cellulose microcrystalline | 400 mg |
| Silicon dioxide fumed | 10 mg |
| Stearic acid | 5 mg |
| Total | 665 mg |

The components are blended and compressed to form tablets each weighing 665 mg.

EXAMPLE 13

Suppositories each containing 25 mg of active ingredient are made as follows:

| | per suppository |
|---|---|
| 1-[bis(4-trifluoromethylphenyl)-imidazol-4(5)-ylmethyl]imidazole | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 14

Suspensions each containing 5 mg of medicament per 5 ml dose are made as follows:

| | per 5 ml of suspension |
|---|---|
| 1-[bis(4-chlorophenyl)-1,3,4-oxadiazol-2-ylmethyl]-1,2,4-triazole | 5 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 15

An aerosol solution is prepared containing the following components:

|  | Weight % |
| --- | --- |
| 1-[(4-fluorophenyl)(4-chlorophenyl)-1,3,4-thiadiazol-2-ylmethyl]imidazole | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

We claim:

1. A method of inhibiting aromatase in a mammal which comprises administering to said mammal an aromatase inhibiting amount of a compound of the formula

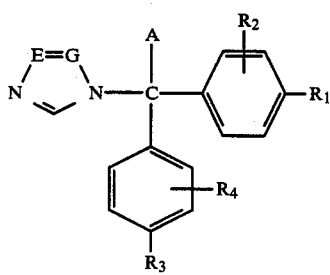

wherein:

A is a 5-membered heterocyclic group containing at least one nitrogen atom beta to the point of attachment selected from the group consisting of 3-pyrrolyl, 4(5)-imidazolyl, 3-pyrazolyl, 4-pyrazolyl, 4-1,2,3-triazolyl, 3-1,2,4-triazolyl, and 5-tetrazolyl;

E and G are independently N or CH; and $R_1$, $R_2$, $R_3$, and $R_4$ are independently hydrogen, halo, nitro, $C_1$–$C_3$ alkyl, $C_1$–$C_3$ alkoxy, or trifluoromethyl; and pharmaceutically acceptable salts thereof.

2. The method according to claim 1 employing a compound wherein $R_1$ and $R_3$ are independently chloro, fluoro, or trifluoromethyl.

3. The method according to claim 2 employing a compound wherein $R_2$ and $R_4$ are each hydrogen.

4. A method of treating estrogen-dependent diseases by inhibiting aromatase in a mammal which comprises administering to said mammal an effective amount of a compound of the formula

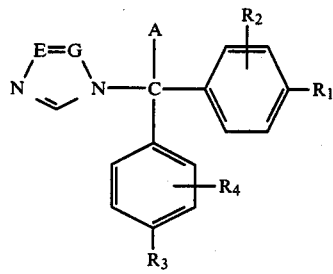

wherein:

A is a 5-membered heterocyclic group containing at least one nitrogen atom beta to the point of attachment selected from the group consisting of 3-pyrrolyl, 4(5)-imidazolyl, 3-pyrazolyl, 4-pyrazolyl, 4-1,2,3-triazolyl, 3-1,2,4-triazolyl, and 5-tetrazolyl;

E and G are independently N or CH; and $R_1$, $R_2$, $R_3$, and $R_4$ are independently hydrogen, halo, nitro, $C_1$–$C_3$ alkyl, $C_1$–$C_3$ alkoxy, or trifluoromethyl; and pharmaceutically acceptable salts thereof.

5. The method according to claim 4 employing a compound wherein $R_1$ and $R_3$ are independently chloro, fluoro, or trifluoromethyl.

6. The method according to claim 5 employing a compound wherein $R_2$ and $R_4$ are each hydrogen.

7. The method according to claim 6 employing 3-[1H-imidazol-1-yl-bis(4-chlorophenyl)methyl]-1,2,4-triazole or a pharmaceutically acceptable salt thereof.

8. A pharmaceutical formulation in unit dosage form useful in the treatment of an estrogen-dependent disease which comprises, per unit dosage, from about 1 to about 500 mg of a compound of the formula

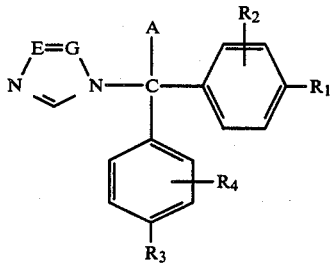

wherein:

A is a 5-membered heterocyclic group containing at least one nitrogen atom beta to the point of attachment selected from the group consisting of 3-pyrrolyl, 4(5)-imidazolyl, 3-pyrazolyl, 4-pyrazolyl, 4-1,2,3-triazolyl, 3-1,2,4-triazolyl, and 5-tetrazolyl;

E and G are independently N or CH; and $R_1$, $R_2$, $R_3$, and $R_4$ are independently hydrogen, halo, nitro, $C_1$–$C_3$ alkyl, $C_1$–$C_3$ alkoxy, or trifluoromethyl; and pharmaceutically acceptable salts thereof in association with a pharmaceutically acceptable carrier, diluent, or excipient therefor.

9. A formulation according to claim 8 employing a compound wherein $R_1$ and $R_3$ are independently chloro, fluoro, or trifluoromethyl.

10. A formulation according to claim 9 employing a compound wherein $R_2$ and $R_4$ are each hydrogen.

11. A formulation according to claim 10 employing 3-[1H-imidazol-1-yl-bis(4-chlorophenyl)methyl]-1,2,4-triazole or a pharmaceutically acceptable salt thereof.

* * * * *